United States Patent
Goodwin et al.

(10) Patent No.: US 9,737,624 B2
(45) Date of Patent: Aug. 22, 2017

(54) SYSTEMS AND CONTAINERS FOR STERILZING A FLUID

(71) Applicant: LIFE TECHNOLOGIES CORPORATION, Carlsbad, CA (US)

(72) Inventors: Michael E. Goodwin, Logan, UT (US); Nephi D. Jones, Newton, UT (US); Bradley H. Buchanan, Lopez Island, WA (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 15/042,974

(22) Filed: Feb. 12, 2016

(65) Prior Publication Data

US 2016/0158394 A1    Jun. 9, 2016

Related U.S. Application Data

(63) Continuation of application No. 14/381,551, filed as application No. PCT/US2013/028059 on Feb. 27, 2013, now Pat. No. 9,289,522.

(60) Provisional application No. 61/604,338, filed on Feb. 28, 2012.

(51) Int. Cl.

| | |
|---|---|
| *A61L 2/00* | (2006.01) |
| *G01N 21/00* | (2006.01) |
| *B01D 17/06* | (2006.01) |
| *A61L 2/08* | (2006.01) |
| *A61L 2/26* | (2006.01) |

(52) U.S. Cl.
CPC ............. *A61L 2/087* (2013.01); *A61L 2/007* (2013.01); *A61L 2/26* (2013.01)

(58) Field of Classification Search
CPC ................ A61L 2/00; A61L 9/18; A61L 9/20
USPC ........ 422/22, 24, 44; 250/22, 435, 437–438, 250/455.11, 433; 210/748.08
See application file for complete search history.

(56) References Cited

U.S. PATENT DOCUMENTS

| | | |
|---|---|---|
| 3,780,308 A | 12/1973 | Nablo |
| 3,809,768 A | 5/1974 | Berry |
| 3,968,195 A | 7/1976 | Bishop |
| 4,014,158 A | 3/1977 | Rausing |
| 4,157,723 A | 6/1979 | Granzow et al. |
| 4,201,209 A | 5/1980 | LeVeen et al. |
| 4,209,013 A | 6/1980 | Alexander et al. |
| 4,242,310 A | 12/1980 | Greff et al. |

(Continued)

FOREIGN PATENT DOCUMENTS

| | | |
|---|---|---|
| DE | 199 25 641 A1 | 12/2000 |
| EP | 0 116 362 A2 | 8/1984 |

(Continued)

OTHER PUBLICATIONS

International Search Report dated Sep. 16, 2013, issued in PCT/US2013/028059, filed Feb. 27, 2013.

*Primary Examiner* — Monzer R Chorbaji
(74) *Attorney, Agent, or Firm* — Workman Nydegger

(57) ABSTRACT

A system for sterilizing a fluid includes a sterilization container bounding a fluid flow path that can be coupled with a fluid source. The sterilization container is comprised of one or more polymeric walls. A beam generator is configured to direct a beam of electromagnetic radiation through at least a portion of the fluid flow path of the sterilization container, the beam of electromagnetic radiation being sufficient to sterilize a fluid within the fluid flow path.

19 Claims, 8 Drawing Sheets

(56) References Cited

U.S. PATENT DOCUMENTS

| | | |
|---|---|---|
| 4,265,279 A | 5/1981 | Weikert |
| 4,507,119 A | 3/1985 | Spencer |
| 4,511,359 A | 4/1985 | Vaillancourt |
| 4,521,263 A | 6/1985 | Benin et al. |
| RE32,056 E | 12/1985 | Granzow et al. |
| 4,588,402 A | 5/1986 | Igari et al. |
| 4,631,444 A | 12/1986 | Cheever |
| 4,850,978 A | 7/1989 | Dudar et al. |
| 4,872,974 A | 10/1989 | Hirayama et al. |
| 4,910,435 A | 3/1990 | Wakalopulos |
| 4,944,132 A | 7/1990 | Carlsson et al. |
| 5,009,654 A | 4/1991 | Minshall et al. |
| 5,120,972 A | 6/1992 | Rangwalla et al. |
| 5,141,592 A | 8/1992 | Shaposka et al. |
| 5,194,742 A | 3/1993 | Avnery et al. |
| 5,209,800 A | 5/1993 | Spencer et al. |
| 5,256,229 A | 10/1993 | Spencer |
| 5,352,210 A | 10/1994 | Marrucchi |
| 5,409,841 A | 4/1995 | Chow |
| 5,480,386 A | 1/1996 | Brohy et al. |
| 5,489,783 A | 2/1996 | Kristiansson |
| 5,496,302 A | 3/1996 | Minshall et al. |
| RE35,203 E | 4/1996 | Wakalopulos |
| 5,530,255 A | 6/1996 | Lyons et al. |
| 5,561,298 A | 10/1996 | Cirlin et al. |
| 5,612,588 A | 3/1997 | Wakalopulos |
| 5,656,491 A | 8/1997 | Cassani et al. |
| 5,744,811 A | 4/1998 | Schonberg et al. |
| 5,770,147 A * | 6/1998 | Muller ............... A61M 1/3616 204/193 |
| 5,802,689 A | 9/1998 | Sano |
| 5,855,731 A | 1/1999 | Spencer |
| 5,869,833 A | 2/1999 | Richardson et al. |
| 5,932,132 A | 8/1999 | Plemons |
| 5,962,995 A | 10/1999 | Avnery |
| 6,022,339 A | 2/2000 | Fowles et al. |
| 6,083,587 A | 7/2000 | Smith et al. |
| 6,085,602 A | 7/2000 | Schorn et al. |
| 6,140,657 A | 10/2000 | Wakalopulos et al. |
| 6,576,201 B1 | 6/2003 | Woo |
| 6,596,230 B1 * | 7/2003 | Woo ..................... A61L 2/0011 250/433 |
| 6,696,018 B2 | 2/2004 | Buchanan |
| 6,709,424 B1 | 3/2004 | Knierbein |
| 6,981,794 B2 | 1/2006 | Bibbo et al. |
| 7,111,649 B2 | 9/2006 | Py |
| RE39,657 E | 5/2007 | Wakalopulos et al. |
| 7,264,771 B2 | 9/2007 | Bilstad et al. |
| 7,358,505 B2 | 4/2008 | Woodworth et al. |
| 7,556,066 B2 | 7/2009 | Py |
| 7,739,859 B2 | 6/2010 | Colato et al. |
| 7,832,185 B2 | 11/2010 | Mastio et al. |
| 7,905,257 B2 | 3/2011 | Py |
| 8,448,674 B2 | 5/2013 | Py |
| 2003/0060747 A1 | 3/2003 | Fries et al. |
| 2003/0156973 A1 | 8/2003 | Bilstad et al. |
| 2004/0000648 A1 | 1/2004 | Rissler et al. |
| 2005/0161614 A1 | 7/2005 | Bilstad et al. |
| 2006/0110282 A1 | 5/2006 | Bilstad et al. |
| 2006/0240546 A1 | 10/2006 | Goodwin et al. |
| 2009/0145855 A1 | 6/2009 | Day |

FOREIGN PATENT DOCUMENTS

| | | |
|---|---|---|
| EP | 0 236 107 | 9/1987 |
| EP | 0 366 269 A1 | 9/1989 |
| EP | 0 696 448 A2 | 2/1996 |
| EP | 1 221 318 A2 | 7/2002 |
| EP | 1 352 684 A2 | 10/2003 |
| JP | 2003-290322 A | 10/2003 |
| JP | 2004-236968 A | 8/2004 |
| WO | 01/54739 A1 | 8/2001 |
| WO | 2013/009765 A2 | 1/2013 |

* cited by examiner

SYSTEMS AND CONTAINERS FOR STERILZING A FLUID

CROSS-REFERENCE TO RELATED APPLICATIONS

This application is a continuation of U.S. application Ser. No. 14/381,551, filed Aug. 27, 2014, which is a US nationalization of PCT Application No. PCT/US2013/028059, filed Feb. 27, 2013, which claims priority to U.S. Provisional Application No. 61/604,338, filed Feb. 28, 2012, and which are incorporated herein by specific reference.

BACKGROUND OF THE INVENTION

1. The Field of the Invention

The present disclosure relates to systems, methods, and containers that sterilize fluids using an electron beam.

2. The Relevant Technology

The biotechnology and pharmaceutical industries are increasingly moving towards the use of disposable polymeric containers and tubing in their manufacturing and processing of sterile liquid product. For example, newly developed bioreactors, which are used in growing cells or microorganisms, commonly comprise a large polymeric bag-like container that is positioned within a rigid support vessel. The cells or microorganisms are grown within the polymeric bag while polymeric tubing coupled with the container is used for adding and removing material from the container. Once a batch is completed, the polymeric bag and tubing are disposed of and a new bag with tubing is used for the next batch. The use of disposable containers and tubing eliminates or at least minimizes the need for cleaning and sterilizing equipment between batches and helps improve quality control.

Although the use of disposable container systems has simplified production and processing, there are still a number of shortcomings with such systems that need to be addressed. One significant issue relates to sterilization. Many biologics are damaged by heat or chemical sterilization. Consequently sterilization is typically done by mechanical filtration. Filtration may be carried out using a membrane with a pore size of 0.2 $\mu$m. This pore size is small enough that bacteria cannot pass through. If viruses need to be removed, a much smaller pore size of around 20 nm is needed.

Mechanical filtration is often the limiting factor in the flow rate of the sterilization system. The sterilization filters are usually thin membranes made from nitrocellulose or polyethersulfone (PES). The membranes are relatively fragile, which limits the amount of pressure that can be applied. The relatively low pressure and small pore size results in relatively low flow rates. In addition, the filters can be expensive to manufacture and have to be replaced frequently, thereby increasing the cost and complexity of using the system.

Accordingly, what is needed in the art are sterilization systems that avoid the flow restrictions and/or other shortcomings caused by mechanical filters with small pore diameters.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION

The present disclosure relates to systems, methods, and thin film or thin walled containers for sterilizing a fluid. Instead of using a sterilization filter to remove bacteria, the systems and methods sterilize the fluid using an electron beam. The sterilization containers used in the system are configured to provide a fluid flow path with dimensions suitable for receiving the electron beam and ensuring sterilization of the fluid. Because the fluid is sterilized with the electron beam, the costs and difficulties of using a sterilization filter can be eliminated. The filters used in the methods and systems described herein can be non-sterilizing and can therefore have larger pore sizes compared to sterilization filters (e.g., 1 micron vs. 0.2 microns), which can reduce the cost of filtration and improve fluid flow in the system.

Figure 1:
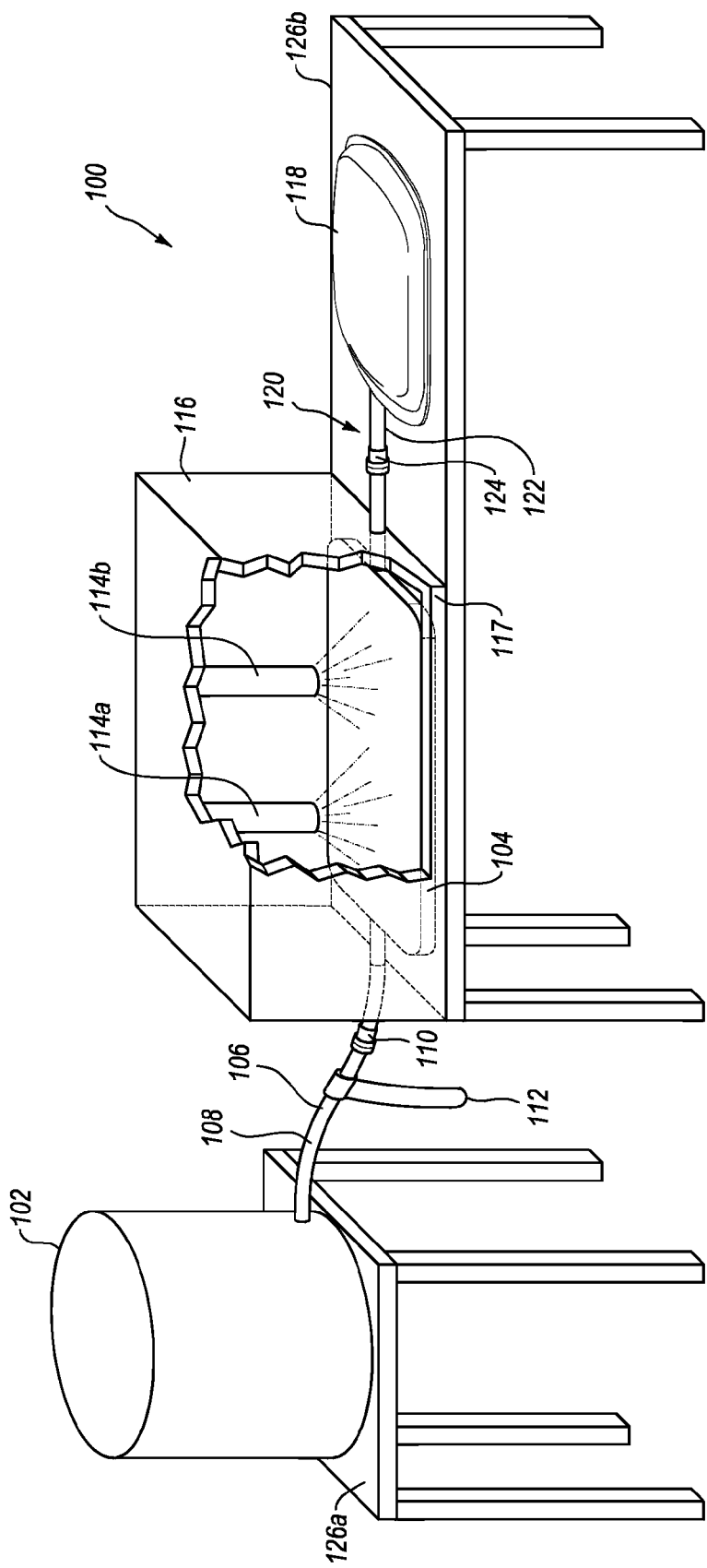
FIG. 1 is a perspective view of a system for sterilizing a fluid using an electron beam.

FIG. 1 illustrates one embodiment of a sterilization system 100 for sterilizing a fluid such as, but not limited to, sterile liquid products produced in the pharmaceutical and biotechnology industries. Examples of such fluids can include media, buffers, reagents, deionized water, Water for Injection, and the like. The fluids can include biologics such as proteins or pharmaceuticals that need to be stored or used in a sterile environment. System 100 includes a fluid source 102 that stores and/or delivers a fluid to be sterilized. Fluid source 102 can comprise a rigid container, such as a stainless steel container that holds the fluid or can comprise a flexible bag, such as a closed bag or an open top liner, that can be supported within a rigid support housing or rest on a support surface. The bag can be a two or three dimensional bag formed from one or more flexible sheets of polymeric film. Fluid source 102 can also comprise a mixing system where the fluid is mixed and/or prepared and can also include a reactor, such as a bioreactor or fermentor.

System 100 includes a sterilization container 104 that is in fluid communication with fluid source 102. As discussed below, sterilization container 104 can comprise a thin film or thin walled container configured to allow sterilization of a fluid therein using an electron beam. Sterilization container 104 may be fluidly coupled to fluid source 102 through a fluid line 106. Fluid line 106 can include flexible tubing 108 or other types of conduits that extend from fluid source 102 to sterilization container 104. One or more connectors 110 can be used to connect fluid line 106 to sterilization container 104. Connector 110 can comprise a non-aseptic connector that requires coupling in a sterile environment or subsequent sterilization or can comprise an aseptic connector, such as the KLEENPAK Sterile Connector produced by the Pall Corporation, which enables sterile coupling in a non-sterile environment. One or more particulate filters 112 can be disposed along fluid line 106 so that the fluid passing from fluid source 102 to sterilization container 104 passes through particulate filters 112. Particulate filters 112 are non-sterilizing filters that have a size cutoff greater than the size of bacteria. For example, particulate filters 112 can be sized to remove material having a size greater than 300 nm, 0.5 micron, 1 micron, 2 microns or other sizes. Often, particulate filters 112 are sized to remove material having a size in a range from 0.5 microns to 2 microns. As a result of removing only relatively large particles relative to sterilizing filters, particulate filters 112 permit higher fluid flow rates than when sterilizing filters are used. Likewise, the inventive system eliminates the cost of sterilizing filters that can be significantly more expensive than non-sterilizing filters. Thus, one embodiment of the present invention can specifically exclude a sterilizing filter located along fluid line 106 having a cutoff of less than 0.5 microns or less than 300 nm.

Sterilization system 100 can also include one or more electron beam generators such as electron beam generators 114a and 114b (collectively electron beam generators 114) that are at least partially disposed within a housing 116. Electron beam generators 114 are configured to generate an electron beam and transmit it into the fluid passing through sterilization container 104, thereby sterilizing the fluid. Electron beam generators 114 can move to scan across one or more desired spots on sterilization container 104 or, alternatively, electron beam generators 114 can be stationary to irradiate a fixed area. In addition, electron beam generators 114 may produce a constant electron beam or a pulsed electron beam and the electron beam may have any impingement pattern suitable for sterilization. The angle of the electron beam may be normal to a support surface on which sterilization container 104 rests or may be at other angles. Where two or more electron beam generators 114 are used, the electron beam generators 114 can be positioned so that the electron beams thereof strike a fluid flow within sterilization container 104 in adjacent parallel alignment and/or consecutively in series. The electron beam generators 114 can simply be placed close enough to each other so that at least portions of the generated beams overlap on the fluid being sterilized or the electron beam generators can be disposed at an angle to one another so that the beams overlap. In other embodiments a single electron beam generator can be used or the electron beam generators can be spaced apart so that the beams do not overlap at the point where they strike the fluid.

Generally, the intensity of the electron beam is selected to ensure sterilization of the fluid while minimizing energy costs and minimizing degradation of non-living desired fluid components such as biologics. Other factors can also be used when determining the intensity of the electron beam. System 100 may include lenses or other devices known in the art to divide, focus, and/or disperse all or a portion of the electron beam to provide a desired impingement pattern of a desired intensity. In addition, a shield gas can be applied between the electron beam generator and the container. The shield gas can comprise a low molecular gas, like helium, that can allow for higher electron energy transfer efficiency to the container and the fluid therein.

Housing 116 provides a protective covering that prevents an operator of the system or others from being exposed to radiation from the electron beam. Housing 116 may be made of any material that has a thickness and composition suitable for reflecting and/or absorbing any extraneous portion of the electron beam. In one embodiment, housing 116 is comprised of stainless steel and tungsten alloys. Other materials can also be used. Housing 116 has a floor 117 or can have an open bottom which rests on a support surface such as table 126. The support surface on which the housing 116 with open bottom would rest would also typically be made of a material suitable for reflecting and/or absorbing any extraneous portion of the electron beam.

The sterilized fluid in sterilization container 104 can be in fluid communication with a storage container 118. Storage container 118 can receive sterilized fluid from sterilization container 104 through fluid line 120, which includes tubing 122 and connector 124. Other configurations for fluid line 120 can also be used. As previously discussed, connector 124 can be an aseptic or non-aseptic connector depending on how the coupling is to be achieved. Since fluid line 120 is downstream from sterilization container 104, fluid line 120 and storage container 118 need to be sterile. It is appreciated that fluid lines 106 and 120 can include any number and/or size of tubing, connectors, and/or filters to deliver fluid from source 102 through sterilization container 104 and into storage container 118. Fluid line 120, which is downstream of sterilization container 104, typically includes sterile components, such as sterile connectors, sterile tubing, and/or sterile filters. Fluid line 106 can include sterile components, but sterile components are not required since contamination in fluid line 106 will be sterilized downstream in sterilization container 104.

Storage container 118 can comprise a flexible bag, such as two or three dimensional bags comprised of one or more flexible sheets of polymeric film, or it can comprise a rigid or semi-rigid vessel, such as a plastic or metal tank. In yet another embodiment, storage container 118 can comprise a manifold system that includes tubing 122 or some other fluid line fluid coupled with a plurality of separate containers, such as flexible bags, that can be filled concurrently or sequentially. One example of a manifold system that can be used in the present invention is disclosed in International Application No. PCT/US2012/046095, filed Jul. 10, 2012 which is incorporated herein by specific reference. System 100 may also include support structures such as, but not limited to, tables 126a and 126b and/or other types of housings, platforms or the like to support or protect the components of system 100.

FIGS. 2-8 illustrate different embodiments of sterilization container 104. The different embodiments of sterilization container 104 provide examples of containers that can be configured to receive an electron beam and ensure sterilization of the fluid disposed therein.

In one embodiment, sterilization container 104 is a thin film container configured to hold a fluid. Specifically, sterilization container 104 can comprise a flexible bag that is comprised of one or more flexible sheets of a polymeric film that is water impermeable, such as a low-density polyethylene. Other flexible sheets of polymeric film having a desired thickness for allowing sterilization of a fluid within the bag using an electron beam can also be used. The material can be comprised of a single ply material or can comprise two or more layers which are either sealed together or separated to form a double wall container. Where the layers are sealed together, the material can comprise a laminated or extruded material. The laminated material comprises two or more separately formed layers that are subsequently secured together by an adhesive.

Figure 7:
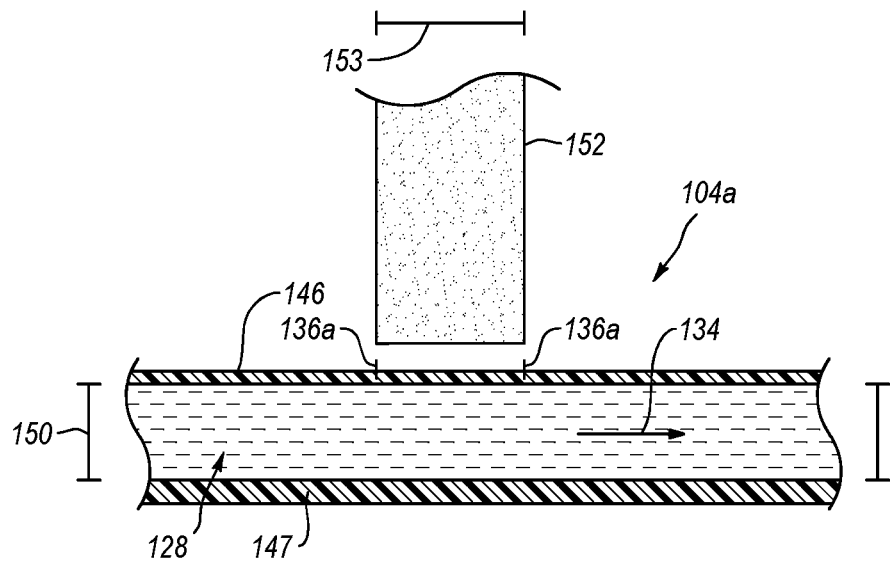
FIG. 7 is a longitudinal cross sectional side view of a fluid flow path in a sterilization container wherein the top wall is thinner than the bottom wall.
Figure 8:
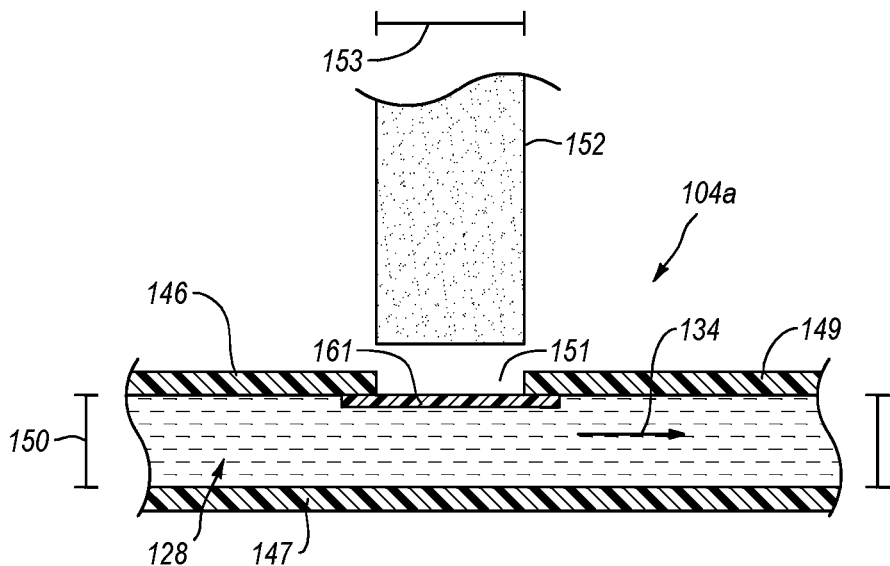
FIG. 8 is a longitudinal cross sectional side view of a fluid flow path in a sterilization container wherein the top wall has a secondary wall portion that is thinner than the remainder of the top wall.

Sterilization container 104 is at least partially made from a thin film having a desired wall thickness in the location where the electron beam impinges (e.g., top wall 146 shown in FIGS. 7 and 8). The wall thickness is the distance between the exterior surface and interior surface of sterilization container 104 which, as discussed above, can include one or more different films or sheets. The thinness of the thin film material is particularly useful for e-beam sterilization because during use container 104 will absorb less of the e-beam energy as compared to a container with a thick wall. This improves the sterilization of the fluid and/or allows the use of a comparatively lower powered e-beam generator. Furthermore, sterilization containers 104 are relatively inexpensive to produce and thus can be disposed of after each use.

In one embodiment sterilization container 104 can have a wall thickness in a range from between about 0.1 mm to about 5 mm with about 0.2 mm to about 2 mm being more common. Other thicknesses or ranges can also be used. Sterilization container 104 can have these wall thicknesses in the location where the electron beam impinges. However, other portions of sterilization container 104 may have the same or different wall thicknesses.

Figure 2:
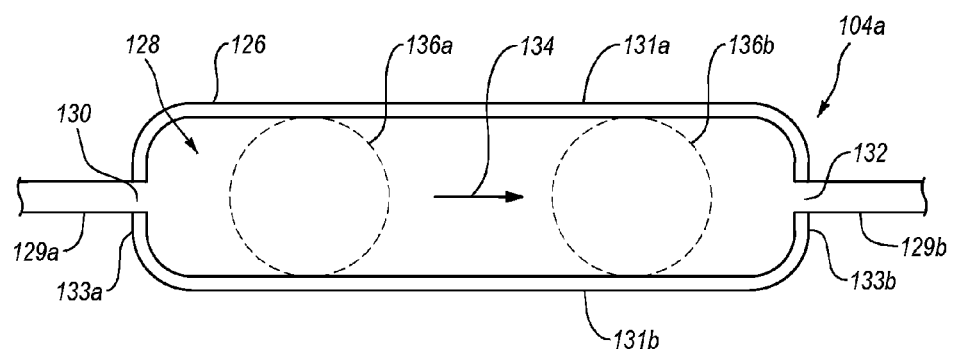
FIG. 2 is a top plan view of a sterilization container having a single fluid flow path.

FIG. 2 illustrates a top view of a sterilization container 104*a* having a body 126 that defines a fluid chamber 128 having a first opening or inlet 130 and a second opening or outlet 132. Fluid lines 129*a* and *b* are in fluid communication with inlet 130 and outlet 132, respectively. Fluid lines 129*a* and *b* can comprise flexible tubing or other types of conduits and can be integrally formed with body 126, welded or otherwise fixed to body 126 or can be secured thereto by a connector, such as an aseptic or non-aseptic connector.

In the embodiment depicted, body 126 is elongated having opposing side edges 131*a* and *b* that longitudinally extend between opposing end edges 133*a* and *b*. Inlet 130 and outlet 132 extend through end edges 133*a* and *b*. In one embodiment, container 104*a* can comprise a two-dimensional pillow type bag where overlying sheets are simply welded along side edges 131*a* and *b* and end edges 133*a* and *b*. Fluid entering inlet 130 and exiting outlet 132 creates a fluid flow path 134 that flows longitudinally through chamber 128. Sterilization container 104*a* is configured to receive a plurality of electron beams covering spots 136*a* and 136*b* (each identified as a dotted circle). Spots 136*a* and 136*b* extend at least to side edges 131*a* and *b* or beyond so that all of the fluid passing through chamber 128 is sterilized. Sterilization container 104*a* can have any number of spots 136 configured to receive an electron beam. While sterilization container 104*a* is shown with two spots, in other embodiments, one, three, or more electron beams can be focused on one, three, or more properly configured spots 136 in chamber 128.

Figure 3:
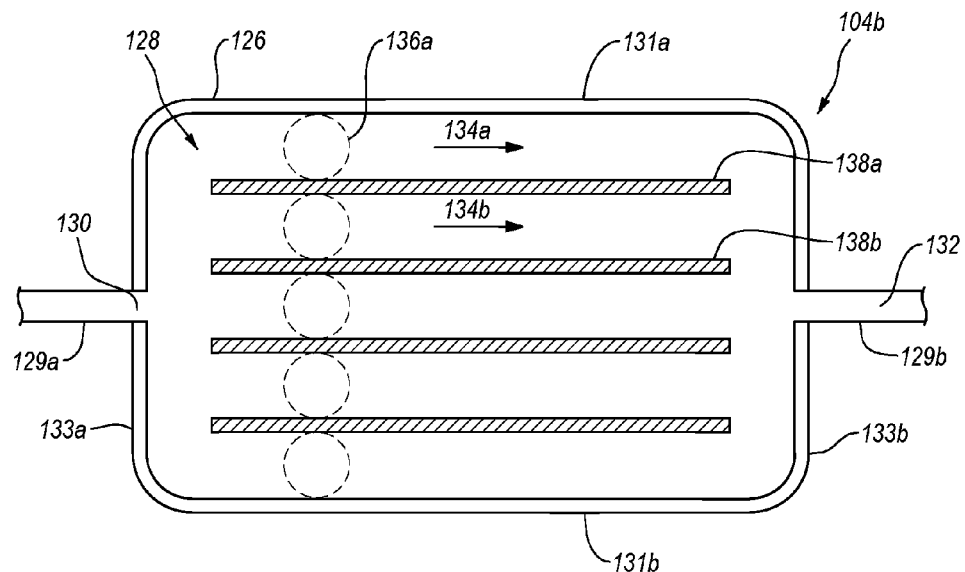
FIG. 3 is a top plan view of a sterilization container having a plurality of fluid flow paths.

FIG. 3 illustrates a sterilization container 104*b* that is similar to sterilization container 104*a*, but includes a plurality of fluid flow paths 134, two of which are identified as fluid flow paths 134*a* and 134*b*. Like elements between containers 104*a* and 104*b* are identified by like reference characters. The plurality of fluid flow paths 134 are produced by a plurality of spaced apart baffles 138 that longitudinally extend along the length of body 126. Baffles 134 do not connect to end edges 133*a* and *b*. This enables fluid passing through inlet 130 to flow into each of the different fluid flow paths 134 and for fluid exiting each of the fluid flow paths 134 to flow into outlet 132.

Fluid flow path 134*a* is formed between side edge 131*a* and a first baffle 138*a*. Fluid flow path 134*b* is formed between first baffle 138*a* and a second baffle 138*b*. The other fluid flow paths 134 are similarly formed. Any number of baffles 138 can be used to divide chamber 128 into any desired number of fluid flow paths 134 having any desired shape or configuration so long as each fluid flow path has at least one spot configured to receive an electron beam and sterilize the fluid therein. For example, the fluid flow paths shown in FIG. 3 each have a spot illustrated by a dotted circle (and identified as dotted circle 136*a* in fluid path 134*a*).

Figure 4:
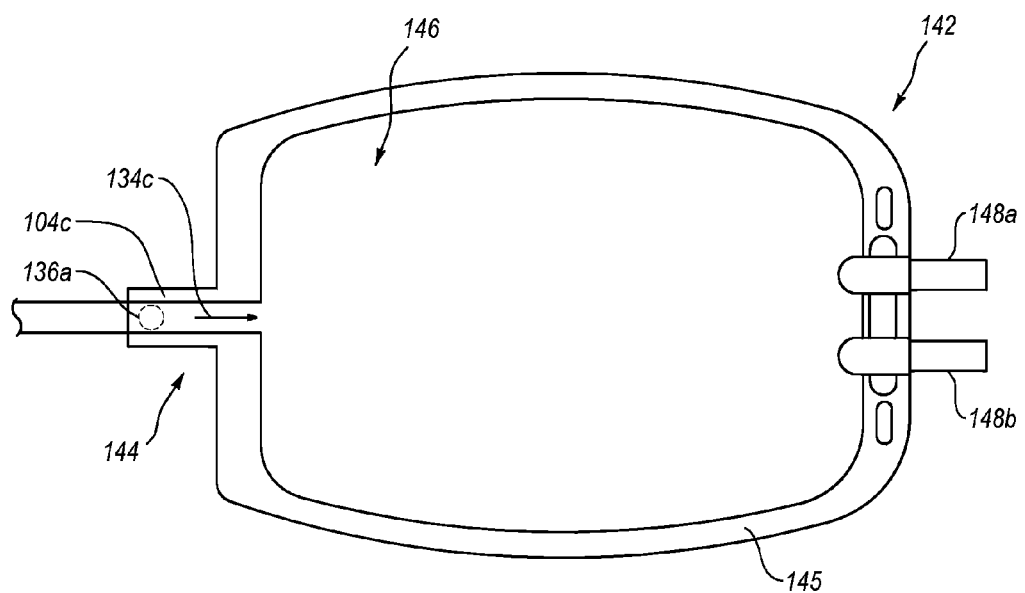
FIG. 4 is a top plan view of a sterilization container incorporated into an inlet of a storage container.

The sterilization containers 104*a* and 104*b* illustrated in FIGS. 2 and 3 may be coupled to fluid source 102 and storage container 118 in the manner shown in FIG. 1 via inlet 130 and outlet 132. However, in an alternative embodiment, sterilization container 104 can be incorporated into a storage container. FIG. 4 illustrates a storage container 142 that includes a body 145 that bounds a chamber 146. Storage container 142 also includes a sterilization container 104*c* in the form of an inlet stem coupled with body 145 and communicating with chamber 146. Sterilization container 104*c* includes a fluid flow path 134*c* having at least one spot 136 configured to receive an electron beam that sterilizes fluid entering chamber 146 of body 145. Body 145 can comprise any type of thin film container or flexible bag comprised of polymeric sheets. For example, body 145 can comprise a gusseted or pillow type bag. Sterilization container 104*c* can comprise an integral portion of the thin film used to form body 145 or can comprise a separate tubular structure that is connected to body 145.

Typically, storage container 142 is initially provided with no voids or minimal voids in chamber 146 and chamber 146 expands as fluid flows through sterilization container 104*c*, where it is sterilized, and then enters chamber 146. Ports 148*a* and 148*b* are tubing that provide fluid communication with chamber 146. Although only a few ports 148*a* and 148*b* are shown, it is appreciated that storage container 142 can be formed with any desired number of ports 148 and that ports 148 can be formed at any desired location on storage container 142. The different ports 148 can be the same configuration or different configurations and can be used for a variety of different purposes. For example, ports 148 can be coupled with fluid lines for transferring fluids or gas into or out of storage container 142.

Ports 148 can also be used for coupling probes to storage container 142. For example, when container 142 is used as a bioreactor for growing cells or microorganisms, ports 148 can be used for coupling probes such as temperature probes, pH probes, dissolved oxygen probes, and the like. Examples of ports 148 and how various probes and lines can be coupled thereto is disclosed in U.S. Patent Publication No. 2006-0240546, published Oct. 26, 2006, which is incorporated herein by specific reference. Ports 148 can also be used for coupling storage container 142 to secondary containers, to condenser systems, and to other desired fittings.

Figure 5:
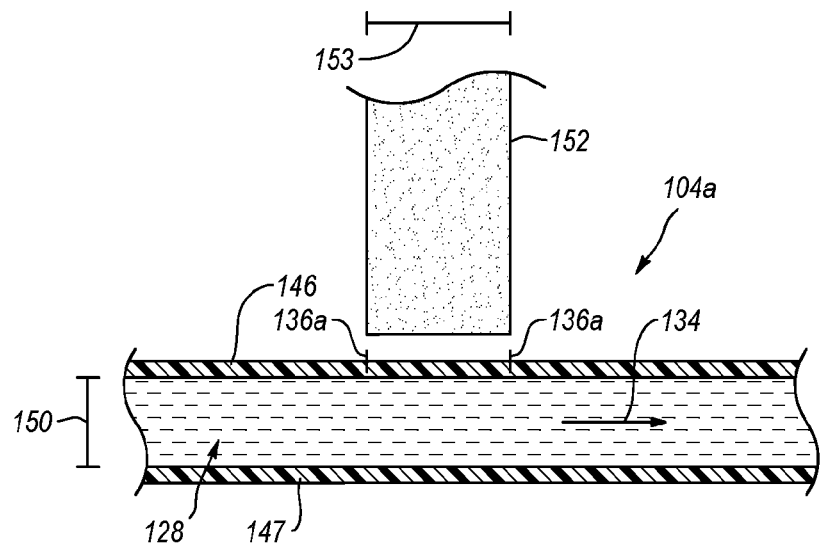
FIG. 5 is a longitudinal cross sectional side view of a fluid flow path in a sterilization container showing sterilization from above.

In order for the fluid flowing through a fluid flow path 134 of a sterilization container 104 to be properly sterilized by an electron beam generator 114, each sterilization container 104 is configured to provide a fluid flow path 134 with a desired thickness when fluid is flowing therethrough. FIG. 5 is a longitudinal cross sectional side view of a portion of sterilization container 104*a*. Sterilization container 104*a* has a top wall or first wall 146 and a bottom wall or second wall 147 that bound the top and bottom of fluid flow path 134 and thus define a vertical thickness 150 of fluid flow path 134, i.e., the thickness at which fluid flows through fluid flow path 134. It is appreciated that because sterilization container 104*a* can be comprised of flexible sheets, the actual thickness of fluid flow path 134 can vary based on factors such as flow rate, fluid pressure, and whether sterilization container 104*a* is secured to a structure. A maximum vertical thickness for a fluid flow path 134 can be measured when the fluid flow path 134 is fully inflated, such as with a liquid or gas, or can be based on the maximum capable thickness for fluid flow path 134 when sterilization container 104 is operating under standard conditions for the system.

The vertical thickness 150 of fluid path 134 is selected to ensure that the electron beam 152 from electron beam generator 114 (FIG. 1) will pass through all of the fluid flowing below spot 136*a* to ensure sterilization. The greater the thickness 150, the more the electron beam will be absorbed by the fluid and the greater the chance that the electron beam will not pass through the entire thickness of the fluid, i.e., reach bottom wall 147, and thus provide the desired sterilization. Preferably vertical thickness 150 at spot 136 where the electron beam traverses the fluid flow path is selected to provide a desired sterilization at a desired flow rate and electron beam intensity. At a given fluid pressure, flow rate increases with increasing thickness and sterilization decreases. In one embodiment, actual vertical thickness 150 (at spot 136*a*) is in a range from about 2 mm to about 4 cm, with about 5 mm to about 3 cm or about 5 mm to about 2 cm being more common. Other dimensions can also be used based on flow rate, beam intensity and other factors. The maximum vertical thickness 150 for the fluid flow path can be in the above ranges or the upper value for the above ranges can increase by 1 cm or 2 cm. For purposes of this invention, the "vertical" direction is determined according to the vector of the electron beam. Thus, where the electron beam is normal to the ground, the vertical measurement will be "up and down." However, an electron beam normal to the ground is not required.

Although spots 136 are shown as being circular (FIG. 2), depending on the configuration of the electron beam generator 114 (FIG. 1), the produced electron beam 152 can have a variety of different cross sectional configurations as it passes through sterilization container 104. For example, electron beam 152 can have a circular, rectangular, square, oval, or other polygonal or irregular transverse cross section. As previously discussed, electron beam 152 needs to have a lateral width (the cross sectional dimension of electron beam 152 extending laterally across the fluid flow) that extends completely across the width of fluid flow path 134 so that all of the fluid flow path is sterilized. Although increasing the lateral width of fluid flow path 134 can increase flow rate and thus decrease processing time, the lateral width of fluid flow paths 134 can be limited based on the electron beam generators 114 that are used and the resulting lateral width of the electron beam 152 that they produce. Thus, in one embodiment the lateral width of fluid flow path 134 and the lateral width of electron beam 152 can be in a range between about 1 cm to about 25 cm with about 2 cm to about 20 cm and about 4 cm to about 15 cm being more common.

If desired, the lateral width of electron beam 152 can be slightly larger than the lateral width of fluid flow path 134 to ensure proper coverage. For example, electron beam 152 can be 1 mm to 3 cm wider than fluid flow path 134. In yet other embodiments, a plurality, such as two, three, or more, of electron beam generators 114 can be aligned laterally across a single fluid flow path 134 having an extended width. The electron beams 152 from these electron beam generators 114 can partially overlap and in combination extend across the full lateral width of the fluid flow path 134. Using this configuration of multiple electron beam generators 114, fluid flow paths 134 of any desired width can be used as long as the thickness of the fluid flow is controlled. One or more electron beam generators 114 can also quickly scan laterally back and forth across fluid flow path 134 for sterilization of the fluid.

The longitudinal width 153 of electron beam 152 (the cross sectional dimension of electron beam 152 along the length of fluid flow path 134) can be the same or different from the lateral width discussed above and is also selected to ensure complete sterilization of fluid passing through spot 136*a* of fluid flow path 134. In general, the wider longitudinal width 153 of electron beam 152, the faster the fluid can be flowed while still achieving sterilization. Alternatively, or in addition to increasing longitudinal width 153, again the number of electron beams 152 (and thus the number of spots 136) incident on fluid flow path 134 can be increased along the length of fluid flow path 134 to ensure complete sterilization at a particular flow rate. The greater the number of incident electron beams with a given beam width, the faster the fluid may be caused to flow while still achieving complete sterilization.

In one embodiment the longitudinal width 153 of electron beam 152 can be in the range between about 1 cm to about 25 cm with about 2 cm to about 20 cm and about 4 cm to about 15 cm being more common. Other dimensions can also be used.

Figure 6:
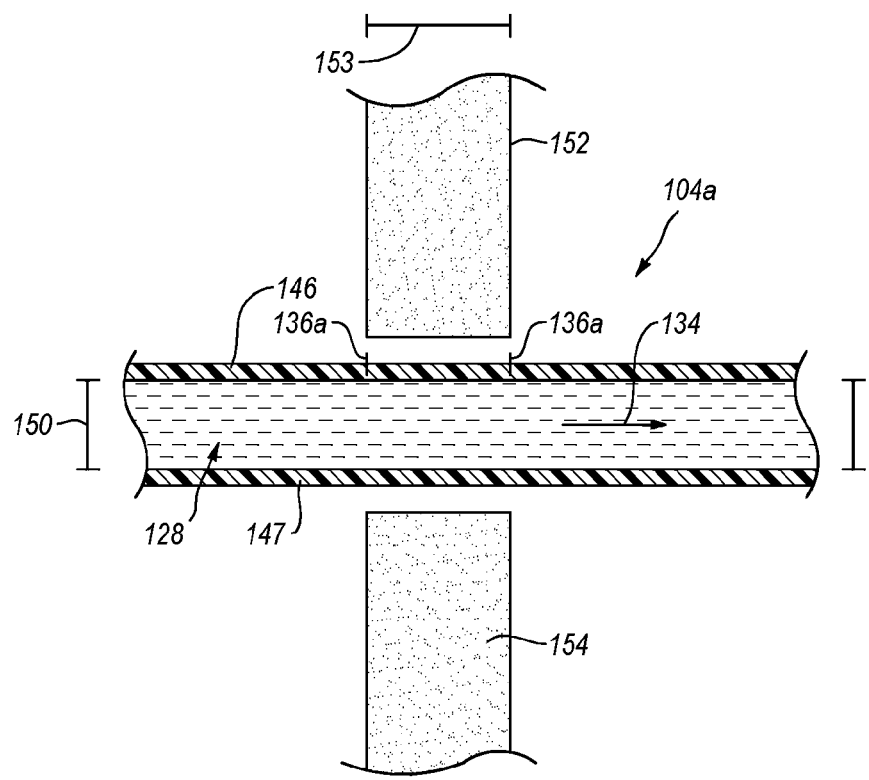
FIG. 6 is a longitudinal cross sectional side view of a fluid flow path in a sterilization container showing sterilization from above and below.

FIG. 6 illustrates an alternative embodiment where a further electron beam generator produces a second electron beam 154 that is directed at spot 136*a* from below fluid flow path 134 and is aligned with electron beam 152. Using second electron beam 154 directed at the bottom wall 147 (in addition to electron beam 152) allows electron beams to sterilize from opposite directions, which provides a greater depth of penetration into the fluid flow path 134. The use of second electron beam 154 allows vertical thickness 150 to be increased and/or provides additional assurance that the fluid will be completely sterilized.

In the embodiment depicted in FIGS. 5 and 6, top wall 146 and bottom wall 147 of sterilization container 104*a* can both have the same thicknesses. In an alternative embodiment, one of walls 146 or 147 can be thinner than the other wall. For example, as depicted in FIG. 7, top wall 146 through which the electron beam(s) are initially passed can have a wall thickness within the ranges as previously discussed. In contrast, however, bottom wall 147 can have a thickness that is at least 10%, 20%, 40% or 60% greater than the thickness of top wall 146. Bottom wall 147 can be thicker because electron beams need not pass therethrough. However, by making bottom wall 147 thicker, sterilization container 104 has greater stability.

Figure 9:
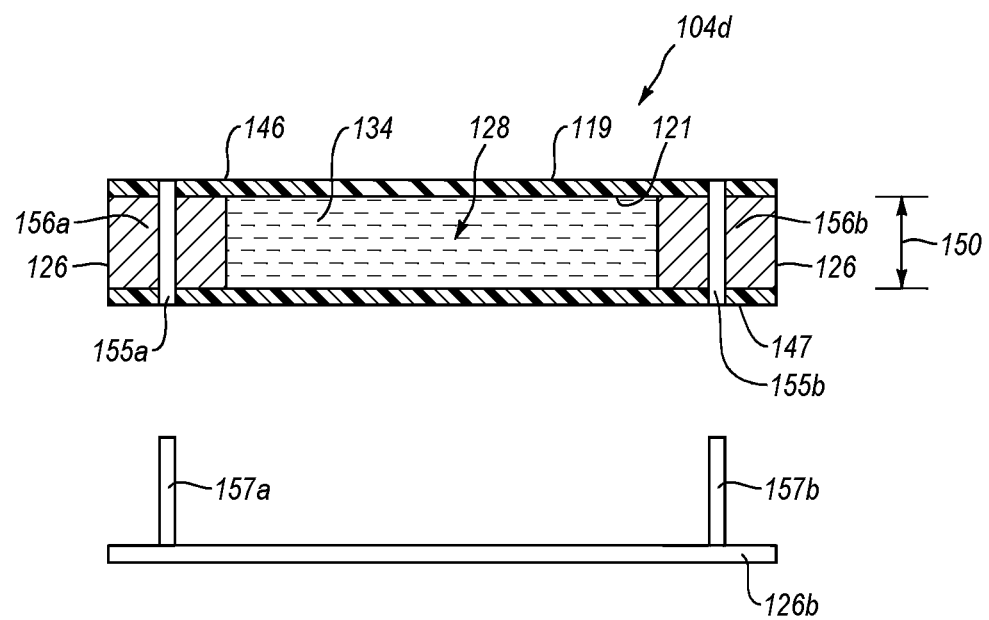
FIG. 9 is a lateral cross sectional side view of a fluid flow path in a sterilization container showing spacers that determine fluid flow path thickness.

In another embodiment as depicted in FIG. 8, container 104a can be formed having top wall 146 and bottom wall 147 wherein top wall 146 includes a primary wall portion 149 having an opening 151 formed therethrough. Opening 151 is covered by a secondary wall portion 161 which is welded to or otherwise secured to primary wall portion 149 so as to seal opening 151 closed. Opening 151 is sized and positioned so that the electron beam from electron beam generator 152 can pass through opening 151 and secondary wall portion 161 for sterilizing the fluid within container 104a. Primary wall portion 149 and secondary wall portion 161 can be made of the same film materials as previously discussed. However, secondary wall portion 161 is made of a thin film material so that the electrons can easily pass therethrough while primary wall portion 149 and bottom wall 147 can be made of a film having a thickness that is at least 10%, 20%, 40% or 60% greater than the thickness of secondary wall portion 161. Again, having primary wall portion 149 and bottom wall 147 made of a thicker material provide greater stability. Where electron beams are being applied to both side of container 104a, such as in FIG. 6, openings with corresponding secondary wall portions can also be made on bottom wall 147. It is appreciated that for each of the sterilizing containers disclosed herein that are made from a film material that the modifications as discussed above with regard to FIGS. 7 and 8 are also applicable thereto. Vertical thickness 150 of fluid flow path 134, as shown in FIGS. 5 and 6, can be selected and/or controlled in various ways and the present invention includes means for limiting the vertical thickness 150. For example, FIG. 9 shows a lateral cross section of a sterilization chamber 104d including a chamber 128 and fluid flow path 134. Sterilization container 104d may be similar to sterilization chamber 104a. In this embodiment, sterilization container 104d comprises an upper wall 146 and an opposing bottom wall 147 and a pair of spacers 156a and 156b secured to and extending along the opposing edges. As discussed above, walls 146 and 147 can each comprise a flexible sheet of polymeric film. Spaces 156a and b can be any desired material but are typically also a polymeric material to which walls 146 and 147 can be easily secured by welding, adhesive, laminating or other conventional techniques. The thickness of spacer 156 helps determine the vertical thickness 150 of fluid flow path 134.

It is appreciated, however, that vertical thickness 150 of sterilization container 104d could be increased if spacers 156a and/or 156b were permitted to move toward each other. In one embodiment, means are provided for immobilizing a sterilization container to minimize expansion of fluid flow path 134. In one example of such means, holes 155a and 155b extend through walls 146 and 147 and/or through spacers 156a and 156b. Pins 157a and b projecting from support table 126 on which sterilization container 104d is positioned can be received within holes 155a and b, respectively, to prevent lateral movement of sterilization container and thereby minimize expansion of fluid flow path 134. In alternative embodiments, pins 157a and b can be replaced by other types of fasteners such as bolts, clamps, clips, and the like for securely holding the sides of sterilization container 104d.

Where chamber 128 includes multiple fluid flow paths, spacers 156 can also be used as baffles. For example, with regard to the embodiment in FIG. 3, spacers 156a and 156b can be used to form side edges 131a and 131b while separate short spacers can be used to form baffles 138.

Figure 10:
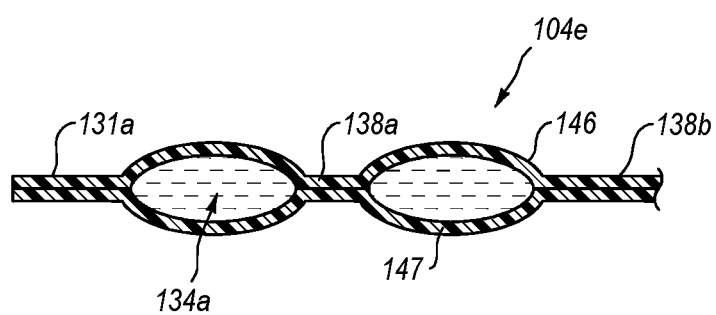
FIG. 10 is a lateral cross sectional side view of a fluid flow path in a sterilization container showing seams that determine the thickness of the fluid flow paths.

In an alternative embodiment, the vertical thickness 150 of fluid flow path 134 can be controlled or limited without the use of a spacer by securing the top wall of the sterilization container directly to the bottom wall thereof at desired locations. FIG. 10 illustrates a lateral cross section of a portion of a sterilization container 104e having a similar construction as sterilization container 104b (FIG. 3). Sterilization container 104e includes top wall 146 and opposing bottom wall 147, as discussed above. Side edge 131a and baffle 138a are formed by securing top wall 146 to bottom wall 147 at spaced apart locations along the length of sterilization container 104e. Side edge 131a and baffle 138a are formed by techniques such as welding, adhesive, laminating, or the like. The welding can be carried out using RF welding, heat welding, or any other suitable technique known in the art. By selecting the spacing between adjacent seams, the vertical thickness of the fluid flow paths can be controlled.

Figure 11:
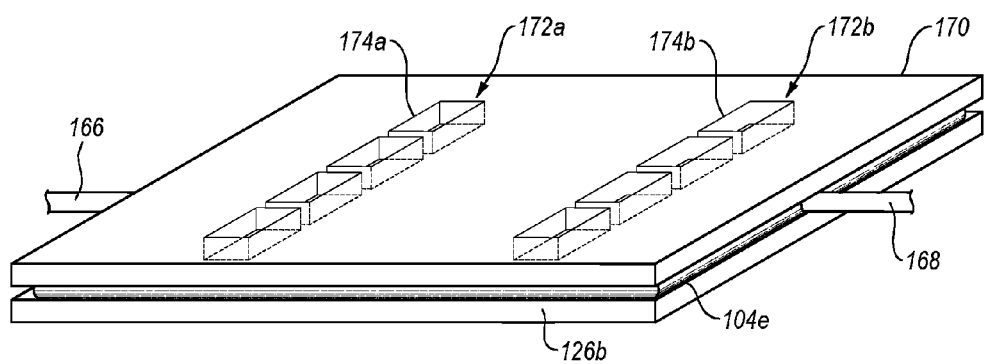
FIG. 11 is a perspective view of a plate positioned on a sterilization container to control the thickness of the fluid flow path therein.

In yet another embodiment, the vertical thickness of fluid flow path can be controlled or limited by using a retention plate that flattens or maintains a desired thickness in the thin film sterilizing container. FIG. 11 illustrates a sterilization container 104e having an inlet 166 and an outlet 168 that allows fluid to be passed within and through sterilization container 104e. Sterilization container 104e can be placed on support 126b or any other type of support and a retention plate 170 may be secured directly above sterilization container 104e to prevent container 104e from bulging when fluid is passed through sterilization container 104e, thereby ensuring container 104e and the fluid passing therethrough is maintained at a desired thickness.

To prevent the bulging, retention plate 170 is typically made from a rigid or semi-rigid material. Retention plate 170 can rest directly on sterilization container 104e and can use its weight or other applied weight to prevent unwanted bulging. In other embodiments, retention plate 170 can be fixed at a location directly above sterilization container 104e to prevent unwanted expansion. For example, retention plate 170 can be secured to housing 116 (FIG. 1) or can be secured to support 126b with legs that elevate it above sterilization container 104e. Plate 170 can be attached to support 126b using fixed fasteners, adjustable fasteners (e.g., a threaded bolt) and/or can be spaced using spacers or other housings. In another embodiment container 104e can be retained between two retention plates 170 that are held together at spaced apart locations by fasteners, spacers or other types of retainers. In this embodiment, it is envisioned that retention plates 170 could be orientated vertically or at other angles while the electronic beams could be oriented normal to plates 170 or at a desired angle. It is appreciated that retention plate 170 need not always be a thin flat structure. Rather, retention plate 170 can be of any desired thickness or configuration but will typically have at least one flat or generally flat surface to rest against the sterilizing container to prevent outward expansion thereof. In one embodiment, plate 170 can be made from a select material having a defined thickness that will enable the electron beam to pass directly through plate 170 and then through sterilization container 104e for sterilizing the fluid therein. In this embodiment, plate 170 can be made of any type of material, including glass, rigid polymeric materials (e.g., poly (methyl methacrylate)), and the like, that enable electron beams to pass therethrough.

In an alternative embodiment, plate 170 may include one or more rows of e-beam windows (e.g., rows 172a and 172b). Each row 172 may include a plurality of windows (e.g., windows 174a and 174b, collectively "windows 174"). Windows 174 provide openings in plate 170 where an e-beam may be directed through sterilization container 104e to sterilize a fluid therein. Providing windows in plate 170 prevents the e-beams from being absorbed by plate 170. This allows plate materials to be used that are not compatible with an e-beam or that would impede sterilization. E-beam windows 174 may be positioned at any location on plate 170 that will align over a fluid flow path. The e-beam windows 174 may be aligned with spots on the sterilization container where the container is configured for sterilization (e.g., container 104e may include a plurality of channels formed similarly to container 104b shown in FIG. 3).

Figure 12:
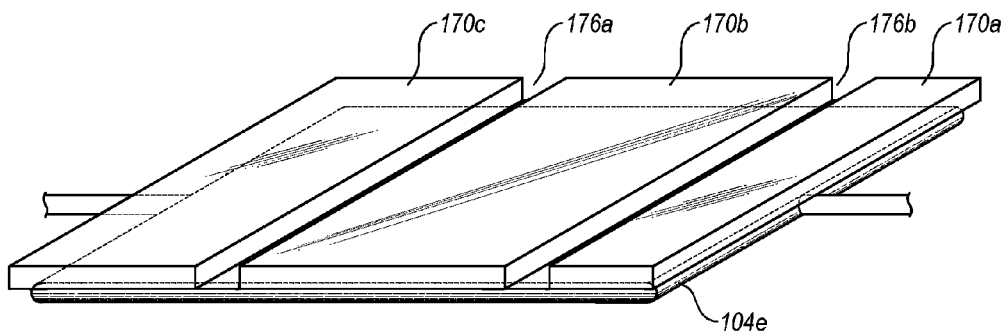
FIG. 12 is a perspective view of a plurality of plates positioned on a sterilization container to control the thickness of the fluid flow path therein.

In another alternative embodiment depicted in FIG. 12, a plurality of retention plates 170a, 170b, and 170c may be used to control the vertical thickness of sterilization container 104e. The plurality of plates 170 can be spaced to provide a plurality of gaps 176a and 176b spanning a portion of sterilization container 104e where one or more electron beams can be focused to sterilize a fluid in sterilization container 104e. The use of continuous gaps allows for sterilization of fluid in the sterilization container 104e where the beam is focused on or scans across a continuous path across sterilization container 104e. This configuration can be useful for sterilizing fluids using fluid container 104a illustrated in FIG. 2.

While plates used to ensure proper vertical thickness can include cutouts such as beam windows or gaps between plates, these cutouts are not required. As mentioned above, in some embodiments a plate can be made sufficiently thin that the e-beam may pass through the plate and carry out sterilization of a fluid disposed within the sterilization container. If the e-beam is transferred through the plate, some amount of energy may be lost. However, in some embodiments, the plate can be sufficiently transparent to the e-beam to allow sterilization of the fluid within. A plate that is exposed to the e-beam may be replaced periodically since the e-beam may degrade the plate over time.

The plates described herein for controlling the vertical thickness of the sterilization container may be used in combination with any of the sterilization containers described herein.

The sterilization containers 104 and/or the storage container 118 discussed herein can be made from flexible films that are biocompatible and/or suitable for use in storing biologics. In one embodiment, the sterilization container 104 and/or the storage container 118 may be a material suitable for extrusion, casting, and/or blow molding. The extruded material may include a single integral sheet that comprises two or more layers of different materials that can be separated by a contact layer. All of the layers may be simultaneously co-extruded. One example of an extruded material that can be used in the present invention is the HyQ CX3-9 film available from HyClone Laboratories, Inc. out of Logan, Utah. The HyQ CX3-9 film is a three-layer, 9 mil cast film produced in a cGMP facility. The outer layer is a polyester elastomer coextruded with an ultra-low density polyethylene product contact layer. Another example of an extruded material that can be used in the present invention is the HyQ CX5-14 cast film also available from HyClone Laboratories, Inc. The HyQ CX5-14 cast film comprises a polyester elastomer outer layer, an ultra-low density polyethylene contact layer, and an EVOH barrier layer disposed therebetween. In still another example, a multi-web film produced from three independent webs of blown film can be used. The two inner webs are each a 4 mil monolayer polyethylene film (which is referred to by HyClone as the HyQ BM1 film) while the outer barrier web is a 5.5 mil thick 6-layer coextrusion film (which is referred to by HyClone as the HyQ BX6 film).

In one embodiment, sterilization container 104 and/or the storage container 118 may include a material approved for direct contact with living cells and is capable of maintaining a solution sterile. In such an embodiment, the material can also be sterilizable such as by ionizing radiation. Examples of materials that can be used in different situations are disclosed in U.S. Pat. No. 6,083,587 which issued on Jul. 4, 2000 and United States Publication No. U.S. 2003-0077466 A1, published Apr. 24, 2003 which are hereby incorporated by specific reference.

In one embodiment, container 104 or 118 may comprise a two-dimensional pillow style bag wherein two sheets of material are placed in overlapping relation and the two sheets are bonded together at their peripheries to form the internal compartment. Alternatively, a single sheet of material can be folded over and seamed around the periphery to form the internal compartment. In another embodiment, the containers can be formed from a continuous tubular extrusion of polymeric material that is cut to length and is seamed closed at the ends.

In still other embodiments, container 104 or 118 can comprise a three-dimensional bag that not only has an annular side wall but also a two dimensional top end wall and a two dimensional bottom end wall. Three dimensional containers comprise a plurality of discrete panels, typically three or more, and more commonly four or six. Each panel is substantially identical and comprises a portion of the side wall, top end wall, and bottom end wall of the container. Corresponding perimeter edges of each panel are seamed. The seams are typically formed using methods known in the art such as heat energies, RF energies, sonics, or other sealing energies. In alternative embodiments, the panels can be formed in a variety of different patterns.

It is appreciated that container 104 and 118 can be manufactured to have virtually any desired size, shape, and configuration so long as the shape is suitable for the use described herein. Generally sterilization container 104 will have a volume much smaller than storage container 118 and fluid will flow through sterilization container 104 to fill storage container 118. Storage container 118 can have a compartment sized to 10 liters, 30 liters, 100 liters, 250 liters, 500 liters, 750 liters, 1,000 liters, 1,500 liters, 3,000 liters, 5,000 liters, 10,000 liters, or other desired volumes or ranges between any of the above volumes. Container 104 and/or container 118 can also be transparent or opaque and can have ultraviolet light inhibitors incorporated therein.

Although in the above discussed embodiments containers 104 and 118 can have a flexible, bag-like configuration, in alternative embodiments it is appreciated that container 104 and/or 118 can comprise a collapsible container or a semi-rigid container. For example, in contrast to making sterilization containers 104 out of a flexible film, sterilization containers 104 can be molded from a plastic so as to have thicker and more rigid walls. For example, in one embodiment the sterilization containers 104 can be formed by injection molding, rotational molding, blow molding, compression molding or the like. These containers can be made as a single unitary structure or as two or more parts that are secured together such as by welding or adhesive.

In other embodiments, as discussed below in greater detail, sterilization containers 104 can be formed from extruded or otherwise prefabricated sheets of polymeric material that are shaped and secured together. The molded and fabricated sterilization containers will typically be formed from polyethylene, polypropylene, or polyvinylidene difluoride (PVDF). However, other moldable plastics capable of operating under the discussed conditions will also work. The walls of the molded and fabricated sterilization containers 104 will typically have a thickness at the location were the electron beams are passing in a range between about 0.1 mm to about 5 mm with about 0.2 mm to about 2 mm being more common. Other dimensions can also be used. Likewise, other surfaces of such sterilization containers can be thicker.

The molded and fabricated sterilization containers can have substantially the same configurations as the thin film sterilization containers previously discussed herein. For example, in alternative embodiments the upper wall 146 and lower wall 147 of the sterilization containers depicted in FIGS. 5-10 the can be molded walls or walls formed from prefabricated polymeric sheets. Likewise, the sterilization containers depicted in FIGS. 1-4 can also be molded or formed from prefabricated sheets. One of the benefits of making sterilization containers out of a thicker or and/or more rigid plastic is that they bow less or not at all as the fluid to be sterilized passes therethrough. As such, it may not be necessary to use any type of retention plate 170 or other retaining structure against these sterilizing containers to retain the desired thickness 150 of fluid flow path 134 passing through the sterilizing containers. The desired thickness 150 of fluid flow path 134 for molded or fabricated sterilization containers can be the same as that discussed above with regard to sterilization containers formed from flexible film.

Figure 13:
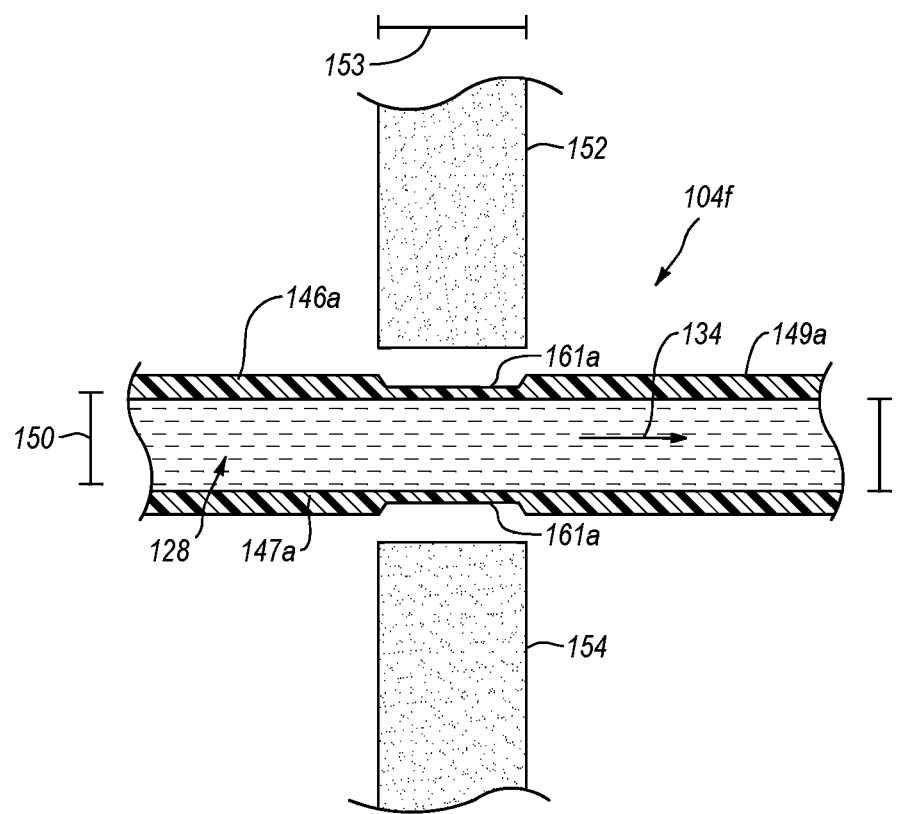
FIG. 13 is a longitudinal cross sectional side view of a fluid flow path in a sterilization container wherein the upper wall and the lower wall are molded with each having a thinned secondary portion.

Depicted in FIG. 13 is one alternative embodiment of a sterilization container 104f made from a molded plastic or prefabricated polymeric sheets. Sterilization container 104f includes a top wall 146a and an opposing bottom wall 147a that bound a fluid flow path therebetween. Top wall 146a has a primary wall portion 149a having a first thickness and a secondary wall portion 161a having a second thickness that is less than the first thickness. Typically, the first thickness is at least 10%, 20%, 40% or 60% greater than the second thickness. Secondary wall portion 161a is designed to align with an electron beam generator 152 and is sufficiently thin so that the electrons can sufficiently pass therethrough for sterilizing the fluid passing through fluid path 134. In contrast, primary wall portion 149a is not designed to have electron beams pass therethrough and has an increased thickness to provide structural support for sterilization container 104f and secondary wall portion 161a. It is appreciated that primary wall portion 149a and secondary wall portion 161a can be integrally molded as a single unitary structure, can be separately welded together, or can be formed by cutting away a portion of the initially formed wall so as to form secondary wall portion 161a. Sterilization container 104f can be formed with any desired number of secondary wall portions 161a and secondary wall portion(s) 161a can be any desired size, shape, or configuration needed for sterilizing the fluid. If electron beams are not being transferred through bottom wall 147a for sterilizing the fluid, bottom wall 147a can be formed having the same thickness as primary wall portion 149a. Otherwise, as depicted in FIG. 13, bottom wall 147a can also be formed with a primary wall portion 149a and any desired number of secondary wall portion 161a. The present disclosure also includes methods for sterilizing a fluid. The methods include passing a fluid through a fluid path formed in a thin film or thin wall container. An electron beam is applied to fluid flowing through the fluid path so as to sterilize the fluid.

The fluid passed through the electron beam can be any fluid in need of sterilization. In one embodiment, the fluid includes a biologic and/or is an aqueous fluid and/or is biocompatible. The fluid to be sterilized can include a biologic such as a peptide and/or small molecule. The fluid to be sterilized can be a fluid useful in the biotechnology or pharmaceutical industry such as growth media and/or other types of fluids that include a biologic.

The fluid is sterilized by passing an electron beam through the fluid. The electron beam can be passed through the fluid at a location where the fluid has a maximum depth that still permits sterilization by the electron beam.

The fluid can be caused to flow at a rate that allows complete sterilization of the fluid. The fluid flow rate can be controlled by selecting the pressure in the sterilization system. The pressure can be a positive pressure upstream from the sterilization container or a negative pressure downstream from the sterilization container. Pressure can be applied using gravity or pumps in a manner known in the art.

Select embodiments of the present invention have unique benefits over the known prior art. For example, select embodiments enable sterilization of a fluid while eliminating the need for sterilization filters. Sterilization filters can be problematic in that they are expensive, can slow fluid flow to decrease production output and require frequent replacement which also slows production. In contrast, the present invention provides a simple, on-demand sterilization process and system that can be easily stopped and started and is designed to maximize throughput. When finished, the sterilization container can be disposed of so that there is no required cleaning or risk of cross contamination. Other benefits also exist.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A system for sterilizing a fluid, comprising:
   a sterilization container bounding a first fluid flow path and being configured to couple with a fluid source, the sterilization container being comprised of a polymeric first wall and an opposing polymeric second wall with the first fluid path being bounded between the first wall and the second wall, the first wall and the second wall each being comprised of a flexible polymeric film;
   a support surface and an adjacently disposed retention plate, the sterilization container being sandwiched between the support surface and the retention plate so that when a fluid passes through the first fluid flow path, the support surface is held stationary relative to the retention plate; and
   a first beam generator configured to direct a first beam of electromagnetic radiation through the polymeric first wall of the sterilization container and through at least a portion of the first fluid flow path, the first beam of electromagnetic radiation being sufficient to at least partially sterilize a fluid when the fluid is passing through the first fluid flow path.

2. The system as recited in claim 1, wherein the sterilization container comprises a collapsible polymeric bag formed from one or more sheets of polymeric film.

3. The system as recited in claim 1, further comprising:
   a second beam generator disposed on a side of the sterilization container that is opposite the first beam generator and is configured to direct a second beam of electromagnetic radiation through the polymeric second wall of the sterilization container and through at least a portion of the first fluid flow path.

4. The system as recited in claim 1, wherein the first beam of electromagnetic radiation is an electron beam.

5. The system as recited in claim 1, wherein the sterilization container is sandwiched between the support surface and the retention plate so that when a fluid passes through the first fluid flow path, the support surface and the retention plate constantly restrain outward expansion of the sterilization container along a fixed length of the sterilization container.

6. A method for sterilizing a fluid comprising:
   passing a fluid through a first fluid flow path of a sterilization container under a pressurized forced fluid flow, the sterilization container being comprised of a polymeric first wall, the first wall being comprised of a sheet of flexible polymeric film; and
   applying a first beam of electromagnetic radiation to the first wall of the sterilization container so that the first beam of electromagnetic radiation passes through the first wall and through at least a portion of the fluid passing through the first fluid flow path of the sterilization container, the first beam of electromagnetic radiation at least partially sterilizing the fluid passing through the sterilization container.

7. The method as recited in claim 6, further comprising passing the fluid through a non-sterilizing, size exclusion filter before passing the fluid through the first fluid flow path of the sterilization container.

8. The method as recited in claim 6, wherein the fluid includes a biologic suitable for use in biotechnology or pharmaceutical applications.

9. The method as recited in claim 6, further comprising dispensing the fluid that passes through the sterilization container into a storage vessel.

10. The method as recited in claim 6, further comprising:
    applying the first beam of electromagnetic radiation to a first side of the sterilization container; and
    applying a second beam of electromagnetic radiation to a second side of the sterilization container that is opposite the first side.

11. The method as recited in claim 6, further comprising:
    passing a fluid through a second fluid flow path of the sterilization container, the second fluid flow path being separated from the first fluid flow path; and
    applying a second beam of electromagnetic radiation to the first wall of the sterilization container so that the second beam of electromagnetic radiation passes through the first wall and through at least a portion of the fluid passing through the second fluid flow path of the sterilization container, the second beam of electromagnetic radiation at least partially sterilizing the fluid passing through the sterilization container.

12. The method as recited in claim 6, further comprising applying means for limiting a thickness of the first fluid flow path to the sterilization container prior to passing the fluid through the first fluid flow path.

13. A container system for use in sterilizing a fluid, the system comprising: a sterilization container having an inlet, an outlet, and a plurality of separate fluid flow paths, each fluid flow path having a first end in fluid communication with the inlet and having a second end in fluid communication with the outlet, the sterilization container being comprised of:
    a first wall comprised of a polymeric material;
    a second wall comprised of a polymeric material; and
    a plurality of elongated baffles, spacers or seam lines formed between the first wall and the second wall, each fluid flow path being separated from the other fluid flow paths by at least one of the baffles, spacers or seam lines.

14. The container system as recited in claim 13, wherein the first wall and the second wall are each comprised of a flexible sheet of a polymeric film.

15. The container system as recited in claim 13, wherein the sterilization container has at least three fluid flow paths.

16. The container system as recited in claim 13, wherein the first ends and the second ends of the fluid flow paths are in fluid communication with each other.

17. A system for sterilizing a fluid, the system comprising:
    the container system as recited in claim 13; and
    a plurality of beam generators each configured to direct a beam of electromagnetic radiation through the first wall of the sterilization container and through at least a portion of a corresponding one of the plurality of fluid flow paths, the beams of electromagnetic radiation being sufficient to at least partially sterilize a fluid when the fluid is passing through the plurality of fluid flow paths.

18. A system for sterilizing a fluid, comprising:
    a sterilization container bounding a fluid flow path and being configured to couple with a fluid source, the sterilization container being comprised of a flexible polymeric first wall;
    a first beam generator configured to direct a first beam of electromagnetic radiation through the flexible polymeric first wall of the sterilization container and through at least a portion of the fluid flow path, the first beam of electromagnetic radiation being sufficient to at least partially sterilize a fluid when the fluid is passed through the fluid flow path; and
    a first retention plate positioned over at least a portion of the flexible polymeric first wall of the sterilization container so as to restrict outward expansion of the first wall when fluid flows through the fluid flow path, an opening being formed either through the first retention plate or adjacent to the first retention plate, the first beam generator being configured to direct the first beam of electromagnetic radiation through the opening.

19. The system for sterilizing a fluid as recited in claim 18, further comprising a second retention plate positioned over a portion of the flexible polymeric first wall of the sterilization container so as to restrict outward expansion of the first wall when fluid flows through the fluid flow path, the opening being formed between the first retention plate and the second retention plate.

* * * * *